United States Patent
Suzuki et al.

(10) Patent No.: US 8,359,905 B2
(45) Date of Patent: Jan. 29, 2013

(54) CERAMIC HEATER AND GAS SENSOR INCLUDING THE SAME

(75) Inventors: Masahito Suzuki, Seki (JP); Tomohiro Kuwayama, Kasugai (JP)

(73) Assignee: NGK Spark Plug Co., Ltd., Aichi (JP)

( * ) Notice: Subject to any disclaimer, the term of this patent is extended or adjusted under 35 U.S.C. 154(b) by 324 days.

(21) Appl. No.: 12/881,311

(22) Filed: Sep. 14, 2010

(65) Prior Publication Data
US 2011/0061444 A1  Mar. 17, 2011

(30) Foreign Application Priority Data

Sep. 15, 2009  (JP) ................ 2009-213250
Aug. 6, 2010  (JP) ................ 2010-177043

(51) Int. Cl.
*G01N 7/00*  (2006.01)
(52) U.S. Cl. ................ 73/31.05; 73/23.31
(58) Field of Classification Search .......... None
See application file for complete search history.

(56) References Cited

U.S. PATENT DOCUMENTS

| 3,136,633 A | | 6/1964 | Berry | |
|---|---|---|---|---|
| 4,839,141 A | * | 6/1989 | Mizuhara | 420/587 |
| 7,078,659 B2 | | 7/2006 | Yokoyama et al. | |
| 2005/0236398 A1 | | 10/2005 | Yokoyama et al. | |
| 2007/0152331 A1 | * | 7/2007 | Kang et al. | 257/737 |
| 2008/0023467 A1 | * | 1/2008 | Sakurai et al. | 219/553 |

FOREIGN PATENT DOCUMENTS

| EP | 1696704 A1 | 8/2006 |
|---|---|---|
| JP | 2005-331502 A | 12/2005 |

OTHER PUBLICATIONS

Communication dated Dec. 8, 2011 from the European Patent Office in counterpart European application No. 10176844.8.

* cited by examiner

*Primary Examiner* — Hezron E Williams
*Assistant Examiner* — Nathaniel Kolb
(74) *Attorney, Agent, or Firm* — Sughrue Mion, PLLC

(57) ABSTRACT

A ceramic heater including: a ceramic substrate having a heater element which generates heat when energized and an electrode pad disposed on a surface of the ceramic substrate, the electrode pad being electrically connected to the heater element, and a connection terminal electrically connected to the electrode pad through a braze part bonded to the electrode pad, the braze part being made of an alloy of copper and gold and the connection terminal being made of nickel or a nickel alloy, wherein a first region of the braze part within a distance of 15 μm from a contact face between the braze part and the connection terminal has a gold content of more than 6 wt % and less than 10 wt %.

4 Claims, 8 Drawing Sheets

CERAMIC HEATER AND GAS SENSOR INCLUDING THE SAME

BACKGROUND OF THE INVENTION

1. Field of the Invention

The present invention relates to a ceramic heater for use in a gas sensor for detecting a gas concentration, and to a gas sensor including the ceramic heater.

2. Description of the Related Art

As an example, an engine may include a gas sensor for detecting a gas concentration (and an air fuel ratio by extension), the gas sensor being provided with a ceramic heater for activating a sensor element.

As such type of ceramic sensor, one obtained by embedding a heater element made of a refractory metal such as tungsten (W) or molybdenum (Mo) in a ceramic substrate of alumina or the like is used. On the outer face of the ceramic heater, an electrode pad electrically connected to the heater element is provided, and a connection terminal used for externally applying a voltage to the heater element is brazed onto the electrode pad with a braze (see, for example, Patent Document 1).

Since a gas sensor is used in a high-temperature environment or an environment with a widely varying temperature in many cases, it is desired to improve, for example, the heat endurance of a part used for brazing (hereinafter also referred to as a braze part) in the ceramic heater. Regarding this point, the heat endurance of the braze part is improved by using a braze alloy including copper. For example, in Patent Document 1, an alloy of copper (Cu) and gold (Au) is used as the braze alloy. Furthermore, the connection terminal is made of an alloy of a nickel (Ni) base with higher corrosion resistance in many cases as described in Patent Document 1.

Patent Document 1: Japanese Laid-Open Patent Publication No. 2005-331502-A

PROBLEMS TO BE SOLVED BY THE INVENTION

In the case where, for example, a connection terminal made of a Ni-based alloy is connected to an electrode pad through a braze part of an alloy (a braze alloy) of Cu and Au, however, a potential difference is generated between the connection terminal and the braze part made of different metals. This is because of a difference between the ionization tendency of Ni and that of Cu and Au. Further, corrosion may result due to this potential difference.

Comparing, for example, the three metals of Ni, Cu and Au with one another, the ionization tendency of Ni is the greatest and hence Ni is more easily oxidized. Also, the ionization tendency of Cu and Au is smaller than that of Ni, and hence Cu and Au are less easily oxidized. In this case, if water or an electrolytic solution enters, for example, an interface between the connection terminal and the braze part, the connection terminal and the braze part function like electrodes of a battery, and therefore, there is a possibility of corrosion of the connection terminal and the braze part.

SUMMARY OF THE INVENTION

The present invention was made in consideration of the above problems of the prior art, and an object thereof is to suppress, in a ceramic heater in which a nickel (Ni)-based connection terminal is connected through a braze part of copper (Cu) and gold (Au) to an electrode pad electrically connected to a heater element, the occurrence of corrosion between the braze part and the connection terminal as compared with that occurring in a conventional ceramic heater.

The above object has been achieved, in accordance with a first aspect (1) of the invention, by providing a ceramic heater which comprises: a ceramic substrate having: a heater element which generates heat when energized; and an electrode pad that is disposed on a surface of the ceramic substrate, the electrode pad being electrically connected to the heater element, and a connection terminal electrically connected to the electrode pad through a braze part bonded to the electrode pad, the braze part being made of an alloy of copper and gold, and the connection terminal being made of nickel or a nickel alloy, wherein a first region (T in FIG. 7) of the braze part that is within a distance of 15 μm from a contact face between the braze part and the connection terminal has a gold content that is more than 6 wt % and less than 10 wt %. The Au content falls in the range of more than 6 wt % to less than 10 wt % throughout the first region.

In a preferred embodiment (2) of the ceramic heater (1) above, the braze part in a second region disposed farther from the connection terminal than the first region has a gold content that is a maximum gold content within the entire braze part.

In accordance with a second aspect (3), the present invention provides a gas sensor comprising: a sensing element having a cylindrical shape and a closed end, said sensing element extending along an axial direction; a metal shell that holds the sensing element; and the ceramic heater (1) above inserted into the sensing element.

In accordance with a third aspect (4), the present invention provides a method for fabricating a ceramic heater including: a ceramic substrate having a heater element which generates heat when energized; an electrode pad disposed on a surface of the ceramic substrate, the electrode pad being electrically connected to the heater element, and a connection terminal electrically connected to the electrode pad through a braze part bonded to the electrode pad, the braze part being made of an alloy of copper and gold and the connection terminal being made of nickel or a nickel alloy, the method comprising: brazing the electrode pad and the connection terminal with each other through a braze alloy made of an alloy of copper and gold to form the braze part; and heating at least the braze part at a temperature lower than a melting point of the braze alloy after the brazing step, wherein a first region of the braze part within a distance of 15 μM from a contact face between the braze part and the connection terminal has a gold content that is more than 6 wt % and less than 10 wt %.

In a preferred embodiment (5) of the method for fabricating a ceramic heater according to (4) above, the braze part in a second region disposed farther from the connection terminal than the first region has a gold content that is a maximum gold content within the entire braze part.

BRIEF DESCRIPTION OF THE DRAWINGS

Illustrative aspects of the invention will be described in detail with reference to the following drawings wherein.

DETAILED DESCRIPTION OF THE PREFERRED EMBODIMENTS

An embodiment of a ceramic heater according to the invention will now be described with reference to the drawings. However, the present invention should not be construed as being limited thereto.

Figure 8:
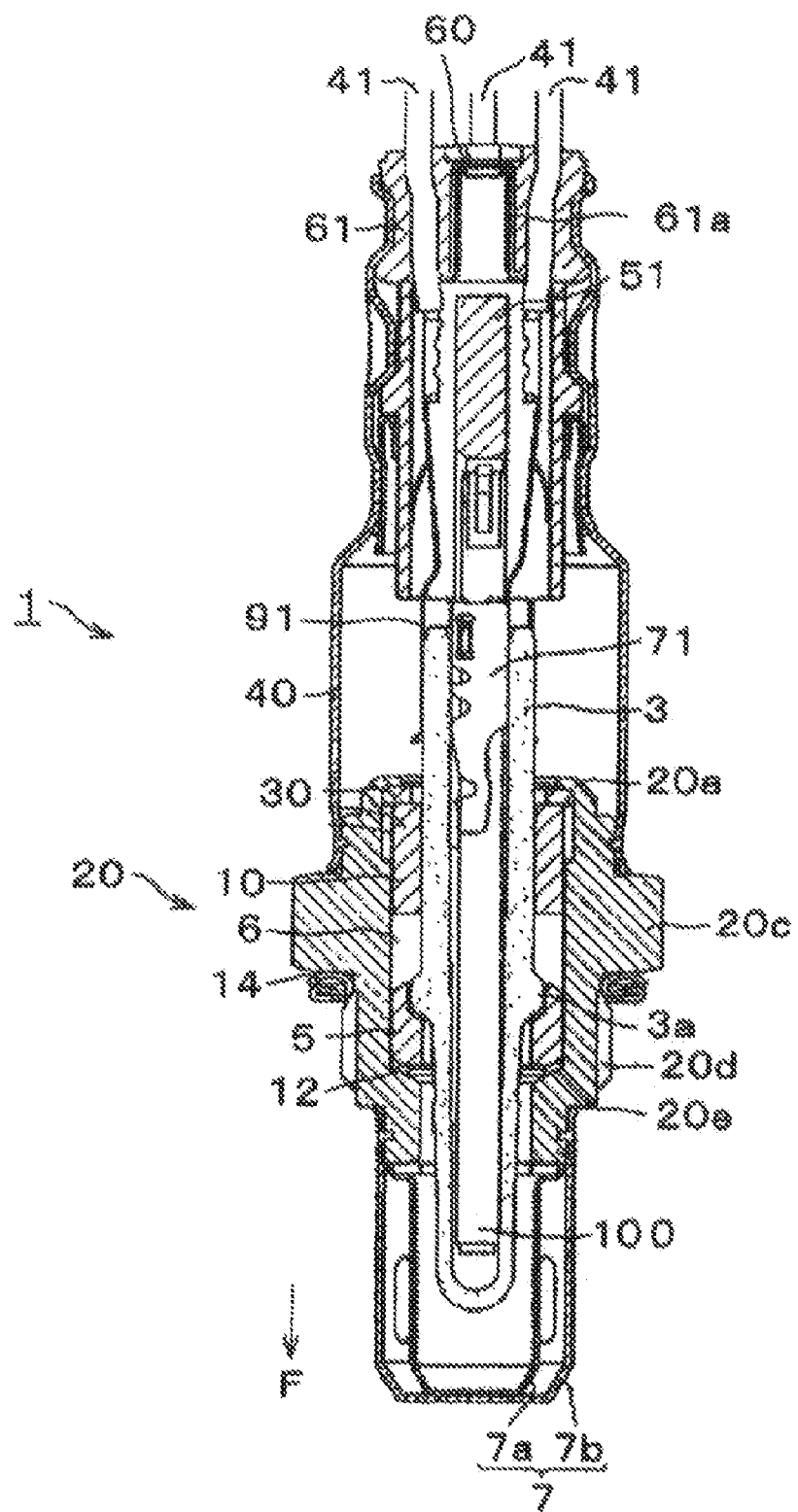
FIG. 8 is a cross-sectional view of a gas sensor 1 according to the embodiment.

The ceramic heater of this embodiment is used in a gas sensor 1 illustrated in FIG. 8. The gas sensor 1 includes a sensor element 3 for detecting a specific gas (oxygen) contained in a measurement target gas (exhaust gas), the gas sensor being used for implementing various control functions (such as air fuel ratio feedback control) in a car, or any of various internal combustion engines.

FIG. 8 is a cross-sectional view taken on a line extending along an axial direction (i.e., a direction from a tip to a base) of the gas sensor 1 of this embodiment. In this embodiment, the gas sensor 1 is inserted into an exhaust pipe of a car with its tip (on a side illustrated with an arrow F in FIG. 8) exposed to exhaust gas for measuring oxygen concentration in the exhaust gas.

In the following description, the lower side (on the side illustrated with the arrow F) of FIG. 8 corresponds to a tip side of the gas sensor 1, and the upper side of FIG. 8 corresponds to a base side of the gas sensor 1.

The gas sensor 1 is an assembly in which the sensor element 3 is attached inside a metal shell 20. The sensor element 3 includes a cylindrically shaped, hollow and closed-end solid electrolyte and an inner electrode and an outer electrode (not shown) formed respectively on an inner face and an outer face of the solid electrolyte. Also, a ceramic heater 100 having a bar shape is inserted into the internal space of the sensor element 3. A flange 3a protruding outward in the radial direction is provided in the vicinity of the center of the sensor element 3.

On the other hand, a polygonal flange 20c protruding outward in the radial direction for engaging a hexagonal wrench or the like and an external thread portion 20d for attaching the metal shell 20 to the exhaust pipe are formed in the vicinity of the center of the metal shell 20. Furthermore, a gasket 14 for preventing gas from leaking when the gas sensor 1 is attached to the exhaust pipe is fit on a tip face of the flange 20c.

Furthermore, a step portion 20e is provided on the inside of the metal shell 20, and a cylindrical ceramic holder 5 is disposed on the base side of the step portion 20e with a packing 12 sandwiched therebetween. Moreover, the flange 3a of the sensor element 3 is in contact with the ceramic holder 5 with a packing (not shown) sandwiched therebetween on the base side.

In addition, a sealing material 6 is filled in a space formed between the sensor element 3 and the metal shell 20 on the base side of the flange 3a, and a cylindrical ceramic sleeve 10 is disposed on the base side of the sealing material 6. With a metal ring 30 provided on the base side of the ceramic sleeve 10, a crimping portion 20a is formed by bending a base side portion of the metal shell 20 inward, and thus, the ceramic sleeve 10 and the sealing material 6 are fixed by crimping.

Moreover, a cylindrical outer casing 40 is connected on the base side of the metal shell 20. The outer casing 40 covers the base side of the sensor element 3, as well as terminal fittings 71 and 91 provided on a base side portion of the sensor element 3. Furthermore, an insulating cylindrical separator 51 is provided inside the outer casing 40, and the terminal fittings 71 and 91 are respectively inserted into and fixed in two insertion holes of the separator 51. Lead wires 41 are respectively connected to the terminal fittings 71 and 91 by crimping.

Also, a cylindrical grommet 61 is fixed by crimping inside a base side portion of the outer casing 40. The grommet 61 is provided with four insertion holes (only two of which are illustrated in FIG. 8) for allowing the lead wires to extend outside. Furthermore, a through hole 61a is formed at the center of the grommet 61, and a water repellent vent filter 60 is provided in the center hole of the grommet 61, so that a standard gas (e.g., air) may be introduced into the internal space of the sensor element 3 without allowing external water to enter.

On the other hand, a cylindrical protector 7 is externally fit on the tip side of the metal shell 20, so that a tip portion of the sensor element 3 protruding beyond the metal shell 20 is covered with the protector 7. The protector 7 has a double structure including an outer protector 7b and an inner protector 7a made of a metal (such as stainless steel) in a closed-end cylindrical shape having a plurality of holes (not shown) and attached to each other by welding or the like.

Next, the structure of the ceramic heater 100 of this embodiment will be described with reference to FIGS. 1 and 2.

Figure 1:
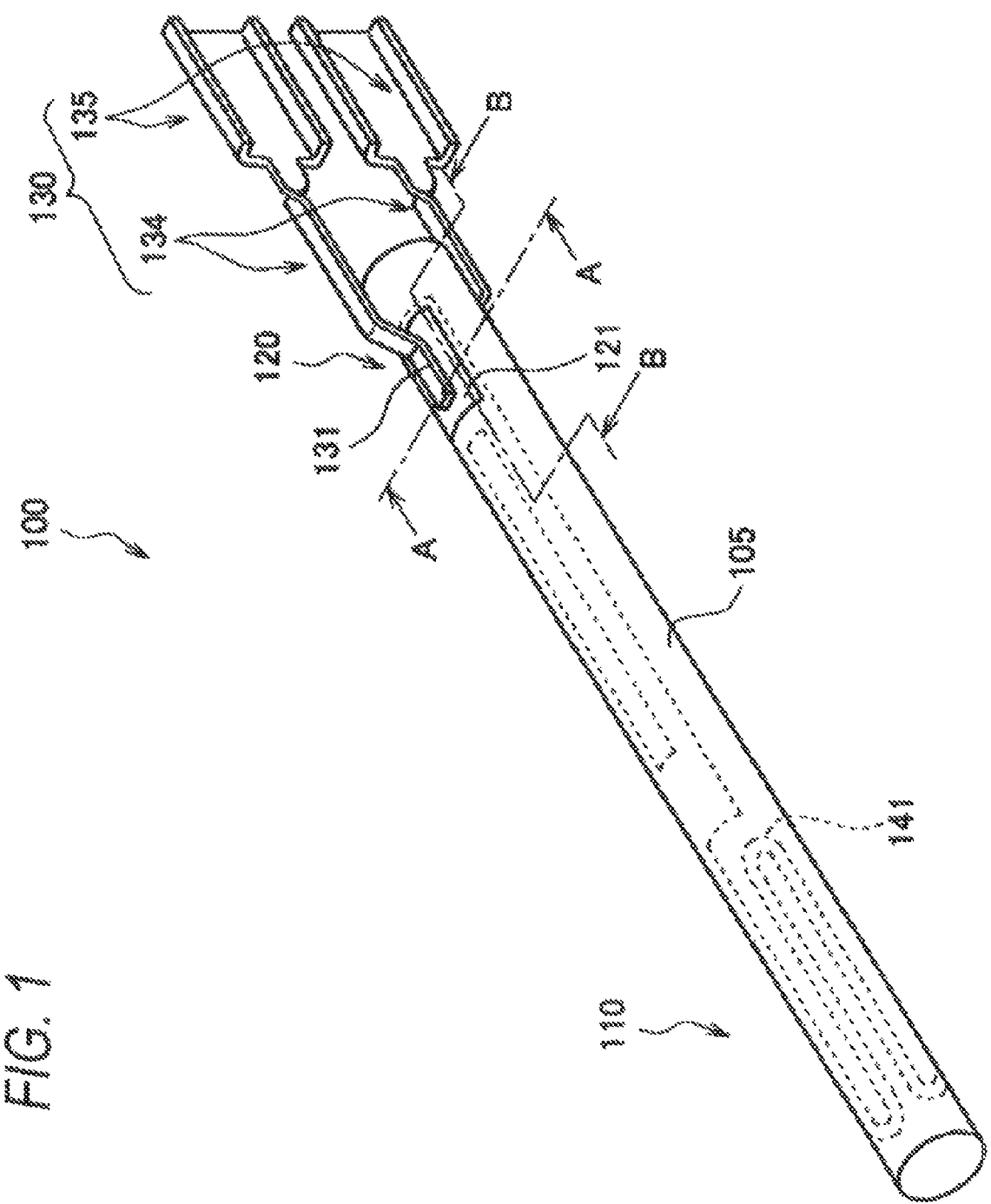
FIG. 1 is a perspective view illustrating a ceramic heater 100 according to an embodiment of the invention.

FIG. 1 is a perspective view illustrating the appearance of the ceramic heater 100. FIG. 2 is an exploded perspective view illustrating the internal structure of the ceramic heater 100. In the following description, a side closer to a heating part 110 (see FIG. 1) of the ceramic heater 100 corresponds to a tip side, and a side closer to an electrode part 120 (see FIG. 1) corresponds to a back side.

As illustrated in FIG. 1, the ceramic heater 100, formed in the shape of a round bar (namely, substantially a circular cylinder), includes a ceramic substrate 105 having a heater element 141; electrode pads 121 exposed on the ceramic substrate 105 for supplying current to the heater element 141; and bonding members 130 connected to the electrode pads 121 with a conductive braze alloy.

The ceramic heater 100 has a structure in which the heater element 141 generates heat by supplying current to the heater element 141 from an external power unit (not shown) through the electrode part 120 provided on the back side of the ceramic substrate 105. A portion for generating heat of the heater element 141 (that is, a heat generating part 142 (see FIG. 2) described below) is disposed on the tip side of the ceramic substrate 105. In other words, the ceramic heater 100 is constructed to heat the sensor element 3 by generating heat by the heating part 110 disposed on the tip side of the ceramic substrate 105.

Figure 2:
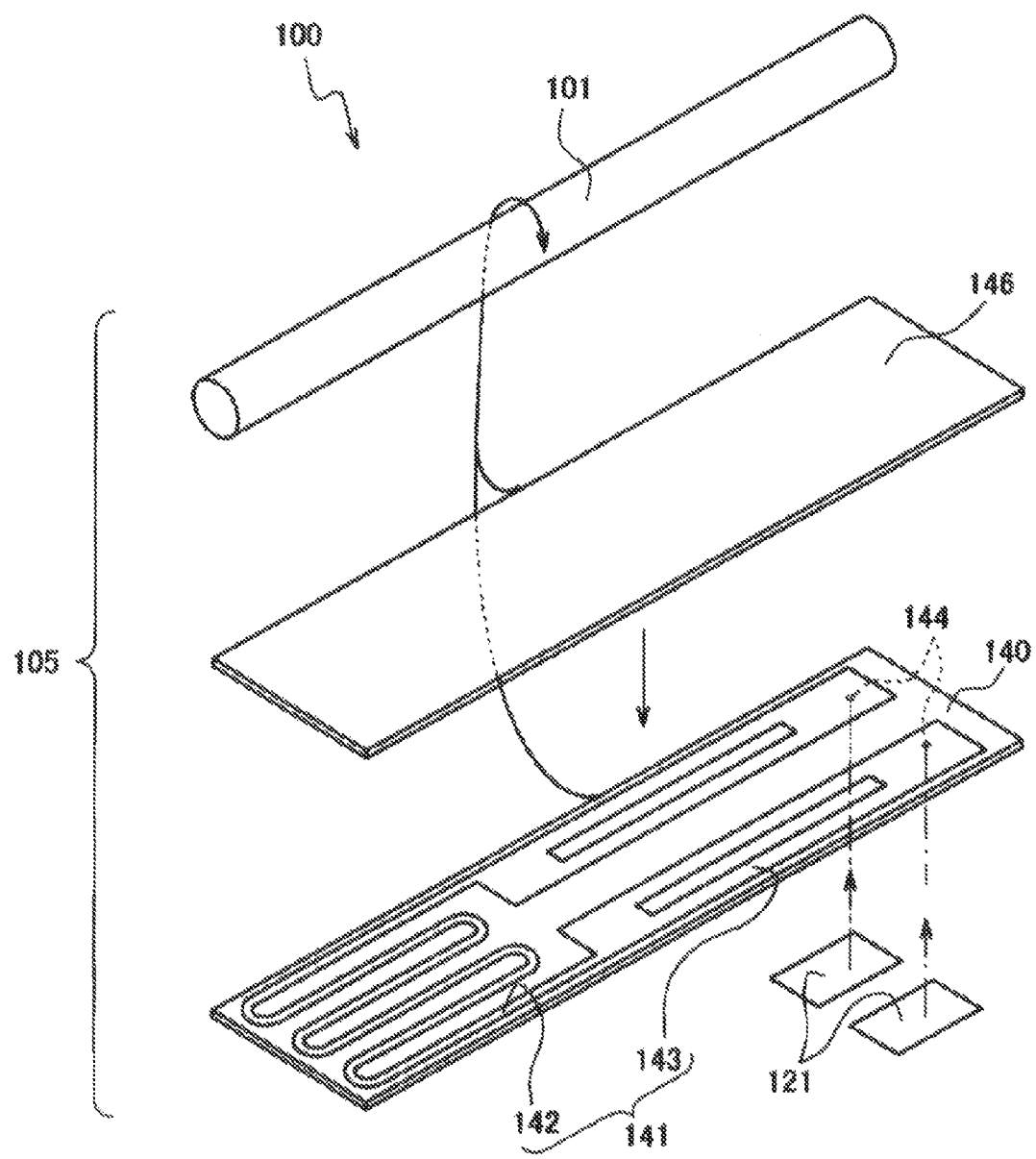
FIG. 2 is an exploded perspective view illustrating the internal structure of the ceramic heater 100 of the embodiment.

As illustrated in FIG. 2, the ceramic heater 100 is fabricated by winding a first sheet member 140 and a second sheet member 146 made of a green sheet of alumina ceramic with a high insulating property around a hollow insulator 101 of alumina ceramic in the shape of a round bar, and by firing the resultant assembly.

On the first sheet member 140, the heater element 141 mainly made of a tungsten (W)-based material is formed as a heater pattern. The heater element 141 includes the heat generating part 142 formed in a position corresponding to the heating part 110 (see FIG. 1), and a pair of lead parts 143 connected respectively to both ends of the heat generating part 142.

Furthermore, two through holes 144 are formed on the back side of the first sheet member 140. The pair of lead parts 143 are respectively electrically connected, through the two through holes 144, to the two electrode pads 121 formed on the outer face of the ceramic heater 100.

Also, the second sheet member 146 is tightly bonded to the face of the first sheet member 140 on which the heater element 141 is formed.

The other face of the second sheet member 146 opposite the first sheet member 140 is coated with an alumina paste, and the first sheet member 140 and the second sheet member 146 are wound around the hollow insulator 101 with the coated face disposed inside and pressed inward from the outer circumferential side, to obtain a ceramic heater molding. Thereafter, the ceramic heater molding is fired, so as to form the ceramic heater 100.

As illustrated in FIGS. 1 and 2, the two electrode pads 121 of an anode side and a cathode side are formed in the electrode part 120 of the ceramic heater 100. The electrode pads 121 are provided in two positions on the outer face of the first sheet member 140 corresponding to the two through holes 144 (see FIG. 2). The electrode pads 121 are electrically connected to the lead parts 143 of the heater element 141 through conductive layers 145 (see FIG. 3 described below) filled in the through holes 144. On each electrode pad 121, a metal plating layer described below (that is, a nickel plating film 122 of FIG. 3 described below) is formed.

Furthermore, in the ceramic heater 100, a bonding part 131 of respective ones of bonding members 130 is brazed onto respective ones of electrode pads 121 through a braze part 124 (see FIGS. 3 and 4 described below) made of an alloy of copper (Cu) and gold (Au).

The bonding member 130 includes a crimping part 135 cut in the shape of a plate and a connecting part 134 extending from the tip of the crimping part 135.

The tip of the connecting part 134 is bent in the thickness direction into a step-like shape, so as to work as the bonding part 131. Furthermore, the bonding member 130 is twisted, in its portion between the connecting part 134 and the crimping part 135, substantially at right angles against the lengthwise direction of the connecting part 134.

Respective ones of bonding members 130 are electrically connected to an external circuit (such as an external power unit not shown) through a lead wire or the like, by crimping, to thereby fix a lead wire for external circuit connection (not shown) onto the crimping part 135.

The two bonding members 130 formed in the aforementioned structure are respectively bonded to the two electrode pads 121, so as to work as an anode terminal and a cathode terminal, respectively, in applying a voltage (i.e., supply current) to the ceramic heater 100.

Next, the structure of the electrode part 120 will be described with reference to FIGS. 3 and 4.

Figure 3:
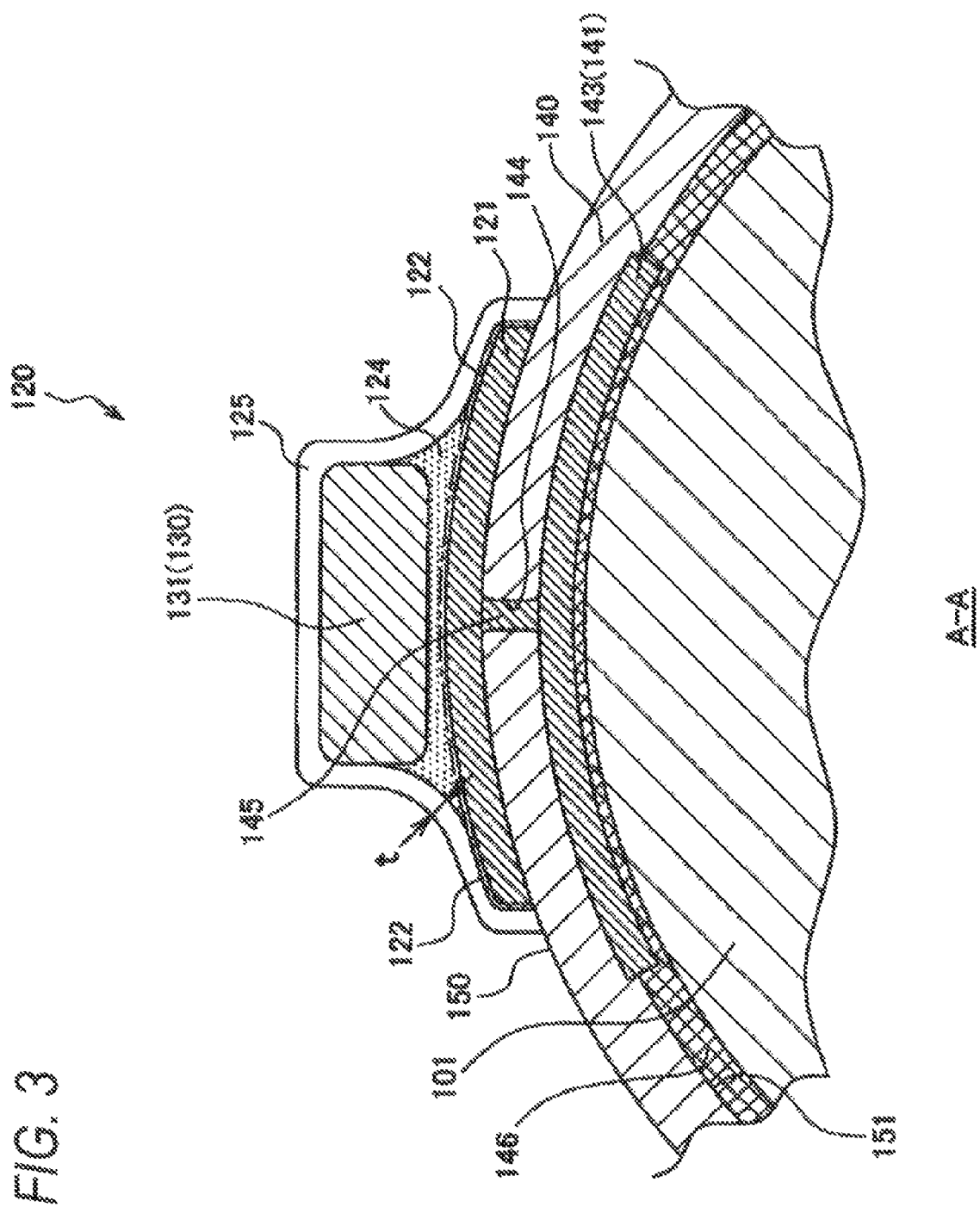
FIG. 3 is a partial cross-sectional view of a peripheral portion of an electrode part 120 (taken on line A-A of FIG. 1)
Figure 4:
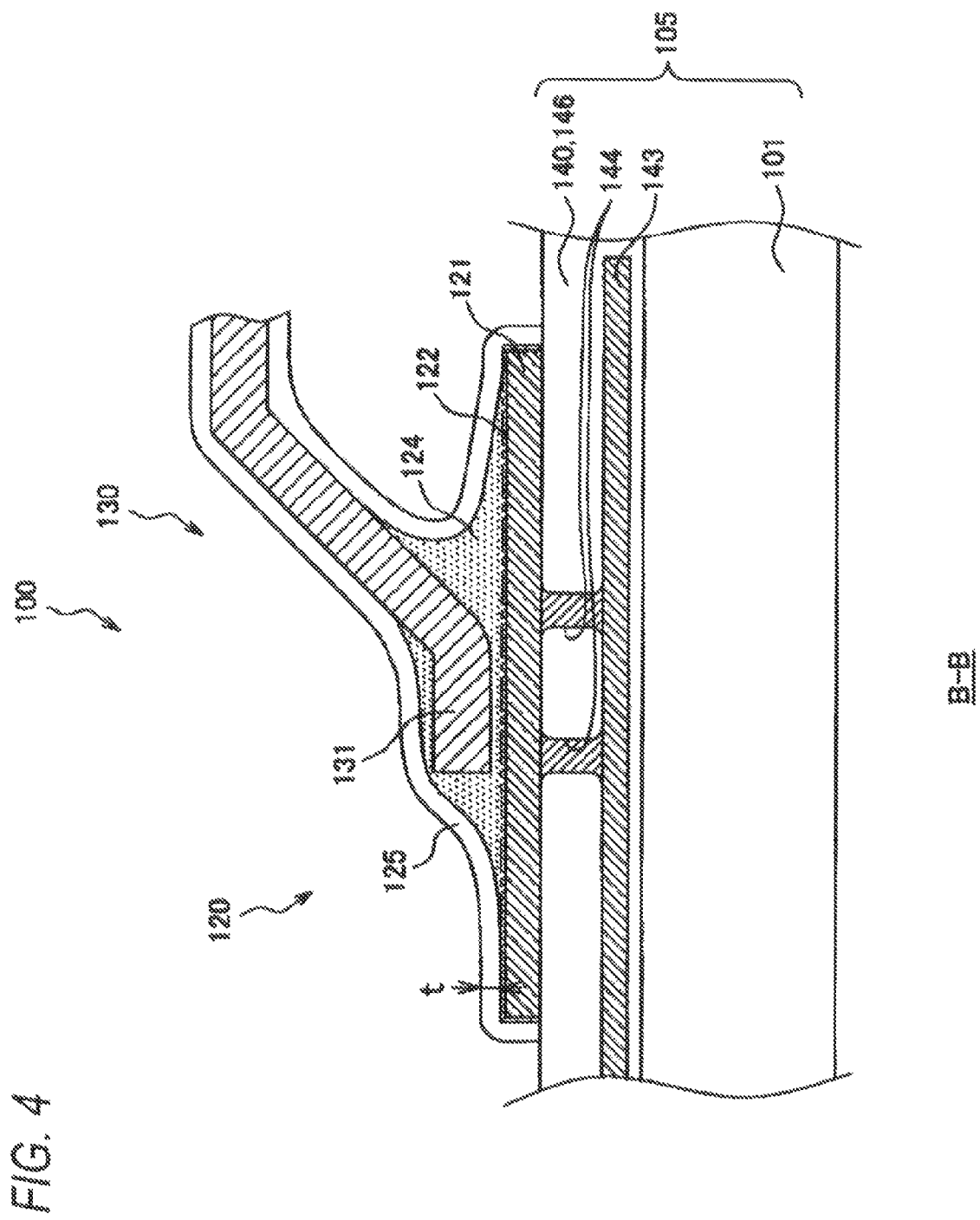
FIG. 4 is a partial cross-sectional view of the peripheral portion of the electrode part 120 (taken on line B-B of FIG. 1)

FIG. 3 is a cross-sectional view of the ceramic heater 100 taken on line A-A of FIG. 1, and FIG. 4 is a cross-sectional view of the ceramic heater 100 taken on line B-B of FIG. 1. These drawings are more specifically partial cross-sectional views of a peripheral portion of the electrode part 120. In the following description, a direction from the bonding member 130 toward the central axis of the ceramic heater 100 in FIGS. 3 and 4 (namely, the downward direction in these drawings) corresponds to a downward direction, and a direction from the central axis of the ceramic heater 100 toward the bonding member 130 (namely, the upward direction in these drawings) corresponds to an upward direction.

As illustrated in FIGS. 3 and 4, the electrode pad 121 formed in the electrode part 120 is formed on an outer face 150 of the first sheet member 140 wound around the hollow insulator 101. Further, the electrode pad 121 is electrically connected to the lead part 143 of the heater element 141 formed on an inner face 151 of the first sheet member 140 through the conductive layer 145 of the through hole 144.

This electrode pad 121 is a metal layer in the shape of a pad including 80 wt % or more of a main material composed of at least one or more elements selected from the group consisting of tungsten (W) and molybdenum (Mo). Tungsten (W) and molybdenum (Mo) are preferably used as components of the electrode pad 121 because they have a good bonding property with the copper-based braze part 124, have a high melting point and have good heat resistance.

The bonding member 130 is made of a nickel member including 90 wt % or more of nickel (Ni).

The bonding part 131 of the bonding member 130 is bonded to the electrode pad 121 through the braze part 124 as illustrated in FIGS. 3 and 4. The braze part 124 is made of an alloy (a braze alloy) of Cu and Au. More specifically, the braze part 124 includes 61 through 72 wt % of Cu and 28 through 39 wt % of Au.

Furthermore, a plating of nickel boron is provided on the bonding part 131 and the electrode pad 121 bonded to each other with the braze part 124, and thus, a nickel boron plating film 125 is formed. The nickel boron plating film 125 is formed to prevent corrosion otherwise caused through oxidation. Electroless plating may be employed for the plating. The electroless plating is also designated as chemical plating, in which a plating layer is obtained without externally supplying electric current. Specifically, metal ions included in a plating solution are reduced by a chemical reducing agent for forming a plating layer. The plating thickness t of the nickel boron plating film 125 is preferably 15 μm or less. FIGS. 3 and 4 schematically illustrate the structure of the electrode part 120, and hence the sizes, the thicknesses and the like of respective portions are not precisely illustrated.

In the ceramic heater 100 of this embodiment having the aforementioned structure, the corrosion resistance of the electrode part 120 is secured by the nickel boron plating film 125. Specifically, if the air, water or an electrolytic solution comes into contact with, for example, the electrode pad 121, the braze part 124 or the bonding part 131, there is a possibility of oxidation or corrosion of the electrode pad 121, the braze part 124 or the bonding part 131. Therefore, the nickel boron plating film 125 prevents air, water or an electrolytic solution from coming into contact with the electrode pad 121, the braze part 124 or the bonding part 131.

Furthermore, a potential difference between different metals is generated particularly between the braze part 124 and the bonding part 131. If water or an electrolytic solution enters a portion between the braze part 124 and the bonding part 131, the braze part 124 and the bonding part 131 function like the electrodes of a battery. Consequently, corrosion may rapidly result or proceed. From this point of view, it is preferred to prevent air, water or an electrolytic solution from coming into contact with the electrode part 120, and to reduce the potential difference generated between the braze part 124 and the bonding part 131.

The potential difference generated between the braze part 124 and the bonding part 131 has been found to vary depending upon the composition ratio (more specifically, the Au content) of the braze part 124. In other words, the composition ratio of the braze part 124 largely affects the corrosion resistance of the electrode part 120 and the ceramic heater 100 by extension.

Figure 5:
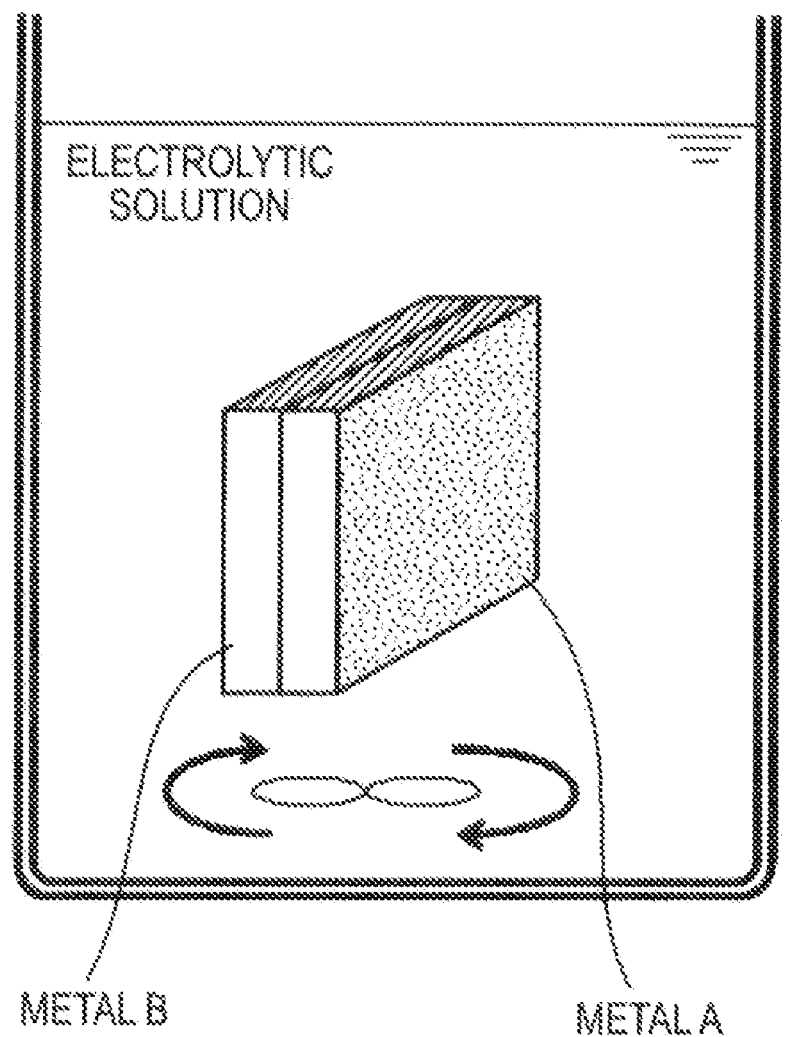
FIG. 5 is a diagram explaining the procedure of an experiment carried out by the present inventors.
Figure 6:
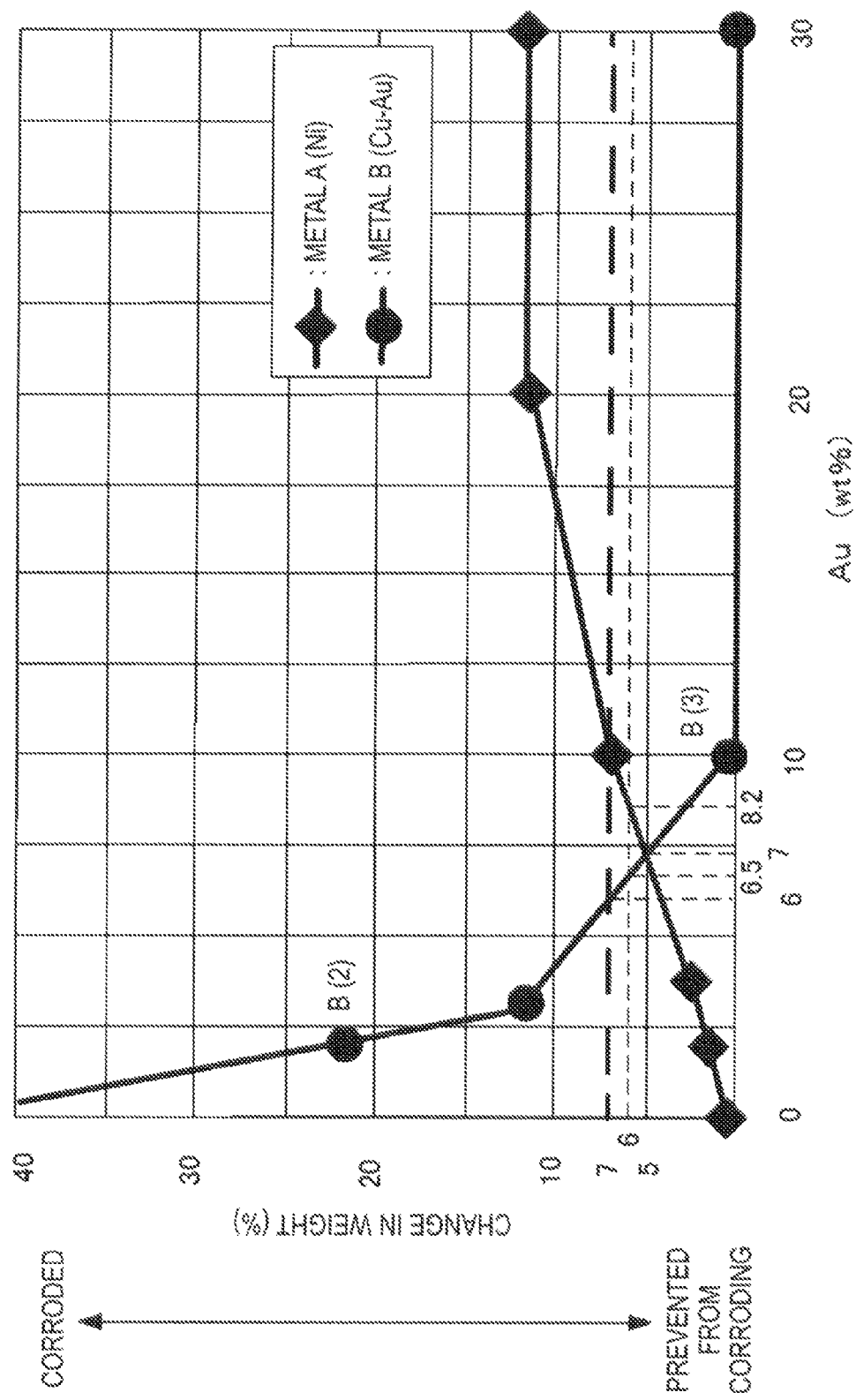
FIG. 6 is a graph illustrating results of the experiment carried out by the present inventors.
Figure 7:
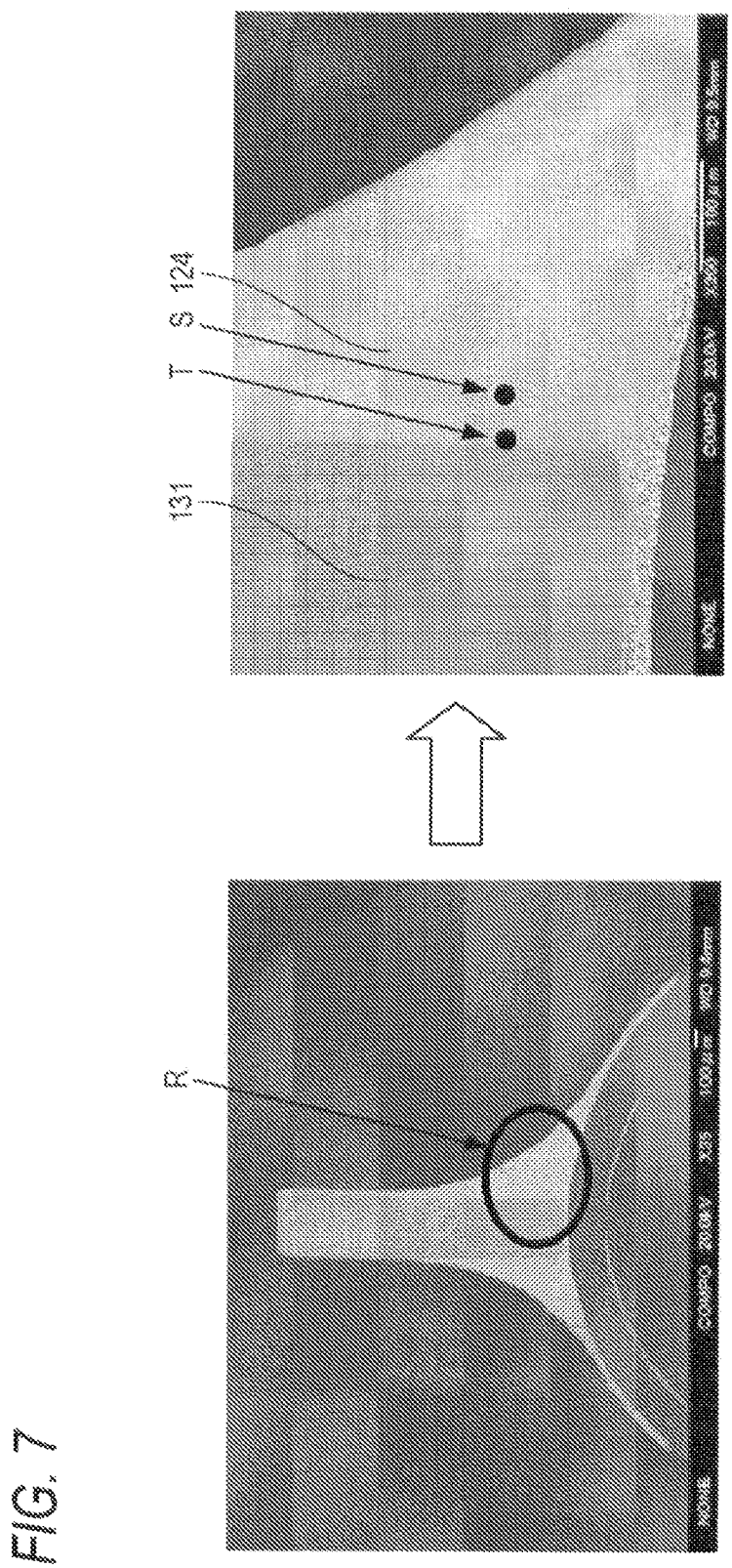
FIG. 7 is a diagram explaining measurement positions for a composition ratio in a braze part 124.

FIGS. 5 through 7 and Tables 1 and 2 below illustrate the procedure and results of experiments carried out by the present inventors, verifying the relationship between the composition ratio of the braze part 124 and the corrosion resistance.

First, FIGS. 5 and 6 will be described.

FIG. 5 is a diagram illustrating the procedure of the experiment. In this experiment, a metal A of Ni corresponding to the bonding member 130 and a metal B of Cu or a Cu—Au alloy corresponding to the braze part 124 are prepared. These metals are overlapped each other and immersed in an electrolytic solution, so as to evaluate the occurrence of corrosion.

As the metal B, a plurality of kinds of metals differing in composition ratio (the content of Au) were used as described in Table 1 below.

Also, the conditions for the experiment illustrated in FIG. 5 will be described in detail with reference to Table 1.

First, as the electrolytic solution, 0.1 wt % (0.027 mol/L) of hydrochloric acid (HCl) was used.

Next, metals A and B will be described. Each of metals A and B was in the shape of a rectangular parallelepiped having a length, a width and a thickness of 33 mm, 33 mm and 0.1 mm, respectively. More specifically, the metal A was pure nickel (namely, having a nickel content of 100 wt %). Also, as metal B, various metals having different composition ratios (differing Au contents) were prepared. Some of these are listed in Table 1 below.

In Table 1, metal B(1) is a metal including Cu alone (namely, having a content of Cu of 100 wt %).

Metal B(2) is a metal including Cu and Au, and particularly having an Au content of 2 wt %.

Metal B(3) is a metal including Cu and Au, and particularly having an Au content of 10 wt %.

Metal B(4) is a metal including Cu and Au, and particularly having Cu and Au contents each of 50 wt %.

Each of various kinds of metals B, including metals B(1) through B(4), was put together with the metal A as shown in FIG. 5, and the metals thus put together were immersed in an electrolytic solution (hydrochloric acid: 0.1 wt % HCl), so as to evaluate the occurrence and resulting extent of corrosion. The metals were immersed in the electrolytic solution for 72 hours, during which time the electrolytic solution was stirred. Furthermore, the experiment was carried out at room temperature. The occurrence and extent of corrosion in the metals A and B were visually evaluated.

TABLE 1

| Electrolytic Solution | HCl 0.1 wt % = 0.027 mol/L | |
|---|---|---|
| Metal | Metal A | Ni (33 × 33 × 0.1 (mm)) |
| | Metal B (1) | 100 wt % Cu (33 × 33 × 0.1 (mm)) |
| | (2) | Cu—2 wt% Au (33 × 33 × 0.1 (mm)) |
| | (3) | Cu—10 wt% Au (33 × 33 × 0.1 (mm)) |
| | (4) | Cu—50 wt% Au (33 × 33 × 0.1 (mm)) |
| Test Time, etc. | 72 hrs. at room temperature | |

Furthermore, with respect to each of metals A and B, a change in weight before and after immersing in the electrolytic solution was measured, and the relationship between the change in weight and the Au content in the metal B was plotted (see FIG. 6).

In the graph of FIG. 6, the ordinate indicates the change in weight and the abscissa indicates the Au content of the metal B. Metals B(2) and B(3) of metals B(1) through B(4) were plotted in accordance with their respective weight changes. Metals B(1) and B(4) were omitted as being outside the range of the graph. Also, in a portion where the gradient of the change in weight changes, the plot points are given separately.

When a metal corrodes, the weight of the metal itself is reduced. This is because, for example, the metal itself dissolves. Therefore, in the graph of FIG. 6, as the change in weight increases, the extent of corrosion is greater. To the contrary, as the change in weight decreases, the extent of corrosion is smaller.

In FIG. 6, when the Au content of the metal B is less than 10 wt %, and as the Au content is decreased (namely, as the Cu content is increased), the change in weight of the metal B becomes greater. In other words, the extent of corrosion becomes greater. This is probably the case because as the Au content of the metal B is decreased, the ionization tendency of the metal B becomes closer to that of Cu. Specifically, the ionization tendency of Cu is larger than the ionization tendency of Au. Hence, when the Au content of the metal B is made smaller, the larger ionization tendency characteristic of Cu becomes pronounced, which seems to explain why corrosion of metal B tends to proceed easily.

For example, with respect to the metal B(2) with an Au content of 2 wt %, the change in weight exceeds 20% (namely, the extent of corrosion is considerable).

Furthermore, when the Au content of the metal B is less than 10 wt %, as the Au content is decreased, the change in weight of the metal A becomes smaller. This is probably the case because metal B is easily corroded as described above. Hence, the corrosion of metal A is suppressed as compared with corrosion of metal B, and as a result, the corrosion of metal A proceeds minimally.

Next, when the Au content of the metal B is not less than 10 wt %, the change in weight of the metal B is approximately 0%, and the extent of corrosion is small. This is probably the case because the ionization tendency of metal B becomes closer to the ionization tendency of Au as the Au content of the metal B is increased. Specifically, the ionization tendency of Au is smaller than the ionization tendency of Cu, and when the Au content of metal B is made larger, the characteristic of Au (namely, its smaller ionization tendency) becomes pronounced, which seems to explain why corrosion only minimally proceeds.

For example, with respect to metal B(3) having an Au content of 10 wt %, the change in weight is 0% and the extent of corrosion is small.

Furthermore, when the Au content of the metal B is not less than 10 wt %, as the Au content is increased, the change in weight of the metal A increases. Metal B is minimally corroded probably because its ionization tendency is smaller as described above, and hence corrosion of metal A proceeds with relative ease.

In addition, the graph of FIG. 6 confirms that the extent of corrosion is large when the change in weight of metal A or the change in weight of metal B exceeds 7%. The results shown in FIG. 6 also confirm that when the change in weight is smaller than 7%, the extent of corrosion of metal A and metal B is small.

The change in weight of metals A and B varies in accordance with the Au content of metal B. Therefore, in order to prevent a change in weight of metals A and B from exceeding 7%, the Au content of the metal B may be controlled. For example, as understood from the graph of FIG. 6, when the Au content of metal B exceeds 10%, the change in weight of metal A exceeds 7%. Also, when the Au content of the metal B is not more than 6%, the change in weight of metal B exceeds 7%. In other words, the Au content of metal B is preferably within a range of from more than 6 wt % to less than 10 wt %.

In this manner, metal A corresponding to the bonding member 130 and metal B corresponding to the braze part 124 were used in the experiment illustrated in FIGS. 5 and 6 so as to check the relationship between the Au content of metal B and corrosion of metals A and B.

Subsequently, an experiment was carried out for verifying the relationship between the composition ratio (the Au content) of the braze part 124, and the corrosion resistance (i.e., possibility of corrosion) of the bonding part 131 and the braze part 124 with the bonding part 131 of the bonding member 130 brazed with the braze part 124. This experiment will be described with reference to FIGS. 7 and 8 and the data of Table 2.

FIG. 7 is a diagram explaining measurement positions for measuring the composition ratio in the braze part 124.

In FIG. 7, the left-hand side photograph is a cross-sectional photograph of the electrode part 120. Also, the right-hand photograph in FIG. 7 is an enlarged photograph of a bonding area (that is, an area illustrated with a reference "R" in the photograph on the left hand side) between the braze part 124 and the bonding part 131.

In the experiment, the composition ratio (more specifically, the Au content) of the braze part 124 was measured at a measurement position T in a first region of the braze part 124. The measurement position T is defined as being within a distance of 15 μm from the interface (the boundary) with the bonding part 131.

Furthermore, the composition ratio (more specifically, the Au content) of the braze part 124 was measured at a measurement position S in a second region of the braze part 124. The measurement position S is defined as being within a distance of 15 μm from the interface (the boundary) between the first region and the second region, namely, a distance of 15 to 30 μm away from the interface (the boundary) with the bonding part 131.

Then, the influence of the composition ratios (i.e., the Au contents) obtained at the measurement positions T and S in the braze part 124 on corrosion resistance was evaluated. Specifically, with respect to each of various composition ratios of the braze part 124 (more specifically, the composition ratios each in an interface region with the bonding part 131) different from one another, the occurrence and the extent of corrosion in the braze part 124 and the bonding part 131 were visually observed.

Table 2 below shows the relationship among local Au contents at the measurement positions T and S (see FIG. 7) in the braze part 124 (listed in the columns of "Au content (T)" and "Au content (S)" in Table 2), overall Au content of the entire braze part 124, and corrosion resistance.

TABLE 2

| Au Content (T): wt % | Au Content (S): wt % | Corrosion resistance | Au Content (entire): wt % | |
|---|---|---|---|---|
| 0 | 0 | corroded in solder part | 0 | (a) |
| 3.4 | 19.1 | corroded in solder part | 15 | (b) |
| 4.2 | 24.8 | corroded in solder part | 20 | (c) |
| 5.2 | 31.5 | corroded in solder part | 25 | (d) |
| 5.8 | 34.6 | corroded in solder part | 27 | (e) |
| 6.1 | 34.7 | no corrosion | 28 | (f) |
| 6.7 | 36.9 | no corrosion | 30 | (g) |
| 8.4 | 44.8 | no corrosion | 35 | (h) |
| 9.5 | 51.6 | no corrosion | 39 | (i) |
| 11.2 | 52.4 | corroded in connection terminal (bonding part) | 40 | (j) |
| 13.8 | 57.2 | corroded in connection terminal (bonding part) | 45 | (k) |

In this experiment, materials (braze alloys) respectively having "Au contents (entire)" of 0 wt %, 15 wt %, 20 wt %, 25 wt %, 27 wt %, 28 wt %, 30 wt %, 35 wt %, 39 wt %, 40 wt % and 45 wt % were prepared. Each of these braze alloys was used for forming a braze part 124. The local Au contents at the measurement positions T and S in each of the thus formed braze parts 124 were measured.

In the following description, composition ratios listed on the first row through the last row of Table 2 are respectively referred to with references (a) through (k).

In each of the composition ratios (a) through (k), the local Au contents measured at the measurement positions T and S are different from the Au overall content in the entire braze part 124 for the following reason:

At a stage of forming the braze part 124, while the braze part 124 is in the form of a fluid before solidifying, Cu present in the second region of the braze part 124 migrates into the first region. More specifically, after the brazing process, when the braze part is heated at a temperature (of 500° C. through 900° C.) lower than the melting point (of, for example, 1060° C.) of the braze alloy, Cu, among Au and Cu included in the braze part 124, tends to concentrate toward the bonding part 131 of Ni. Thus, Cu is made moved by heating from the second region into the first region before the braze part 124 is solidified. Therefore, the Cu content becomes relatively large at the measurement position T, and to the contrary, the Au content becomes relatively small. Furthermore, the Cu content becomes relatively small at the measurement position S, and to the contrary, the Au content becomes relatively large.

In this experiment, ceramic heaters 100 respectively including the braze parts 124 formed to have the composition ratios (a) through (k) shown in Table 2 were fabricated as samples, and a portion corresponding to the electrode part 120 (namely, a portion corresponding to the braze part 124 and the bonding part 131) of each sample, was immersed in an electrolytic solution (i.e., 0.1 wt % HCl=0.027 mol/L HCl), so as to evaluate the occurrence and extent of corrosion. Each sample was immersed in the electrolytic solution for 72 hours, during which time the electrolytic solution was stirred. Furthermore, the experiment was carried out at room temperature.

With respect to the composition ratios (a) through (k), the occurrence of corrosion was evaluated. Corrosion was found in a portion corresponding to the braze part 124 in those samples employing the composition ratios (a) through (e) of Table 2. Also, corrosion was found in a portion corresponding to the bonding part 131 in those samples employing the composition ratios (j) and (k).

On the other hand, corrosion was not found in those samples employing the composition ratios (f) through (i).

More specifically, corrosion was not found when the Au content at the measurement position T of the braze part 124 was more than 6.0 wt % (corresponding to the composition ratio (f)) and less than 10.0 wt % (corresponding to the composition ratio (i)). In other words, it was found that higher corrosion resistance may be attained when the Au content at the measurement position T of the braze part 124 is more than 6.0 wt % and less than 10.0 wt %.

Namely, the following was found: In order to attain an Au content at the measurement position T of the braze part 124 of more than 6.0 wt % and less than 10.0 wt %, the Au content in the entire braze part 124 is set to 28 wt % through 39 wt % as understood from the column "Au content (entire)" of Table 2, and the braze part 124 is heated at a temperature lower than the melting point of the braze alloy after the brazing process.

As understood from the aforementioned experiments, in the ceramic heater 100 including the braze part 124 made of an alloy of Cu and Au and the bonding part 131 made of Ni, when the Au content in the first region of the braze part 124 is more than 6 wt % and less than 10 wt %, higher corrosion resistance may be attained. More specifically, the occurrence of corrosion in the bonding part 131 and the braze part 124 may thereby be suppressed.

In order to attain an Au content in the first region of the braze part 124 of more than 6 wt % and less than 10 wt %, a Cu—Au alloy having an Au content of 28 wt % through 39 wt % is used as a braze alloy for forming the braze part 124, and the thus obtained braze part 124 is heated at a temperature lower than the melting point of the braze alloy after the brazing process. Thus, Cu originally present in the second region migrates into the first region.

Although a preferred embodiment of the invention has been described above, the present invention is not limited thereto. Further, the invention may be embodied in various forms without departing from the gist of the invention. Non-limiting modifications include the following.

For example, the effect of the invention may be attained even when the bonding member 130 is made of Ni having a purity of 100%.

Alternatively, a temperature for brazing the bonding member 130, for example, may be any temperature in the aforementioned embodiment.

Furthermore, in the aforementioned embodiment, when the Au content of metal B compared to the braze part 124 is more than 6.5 wt % and less than 8.2 wt %, the change in weight of metal B and the change in weight of metal A compared to the bonding member 130 may be suppressed to less than 6% as illustrated in FIG. 6. Specifically, when the Au content is more than 6.5 wt % and less than 8.2 wt % in the interface region between the braze part 124 and the bonding member 130 (the bonding part 131), the occurrence of corrosion in the braze part 124 and the bonding member 130 (the bonding part 131) may be further suppressed, resulting in further improvement in corrosion resistance and endurance of the ceramic heater 100. Furthermore, when the Au content of metal B is approximately 7 wt %, the change in weight of metals A and B may be approximately 5% as illustrated in FIG. 6, and thus, the occurrence of corrosion in metal A and metal B (i.e., the bonding member 130 (the bonding part 131) and the braze part 124) may be further suppressed.

As described above, according to the exemplary embodiment, the present invention provides a ceramic heater comprising: a ceramic substrate having: a heater element which generates heat when energized; and an electrode pad disposed on a surface of the ceramic substrate, the electrode pad being electrically connected to the heater element, and a connection terminal electrically connected to the electrode pad through a braze part bonded to the electrode pad, the braze part being made of an alloy of copper and gold and the connection terminal being made of nickel or a nickel alloy, wherein a gold content of in a first region of the braze part within a distance of 15 μm from a contact face between the braze part and the connection terminal is more than 6 wt % and less than 10 wt %. The Au content falls in the range of more than 6 wt % to less than 10 wt % throughout the first region.

A potential difference is generated, due to a difference in ionization tendency, between a connection terminal made of nickel or a nickel alloy (hereinafter also referred to as the Ni connection terminal) and a braze part made of an alloy of copper and gold (hereinafter also referred to as the Cu—Au braze part). In the case where water or an electrolytic solution enters, the Ni connection terminal and the Cu—Au braze part function like the electrodes of a battery, and hence, are subject to corrosion. Therefore, the potential difference between the Ni connection terminal and the Cu—Au braze part is preferably made as small as possible.

The present inventors found that when the Au content of a first region corresponding to a portion of a Cu—Au braze part in contact with a Ni connection terminal is more than 6 wt % and less than 10 wt %, a potential difference generated between the Ni connection terminal and the first region in contact with the Ni connection terminal is minimized. This is probably the case because the ionization tendency is changed in accordance with the contents of the respective components (i.e., Cu and Au) in the first region. Particularly, when the Au content falls in the range of more than 6 wt % to less than 10 wt %, the potential difference generated between the Ni connection terminal and the first region becomes smaller.

Accordingly, in a ceramic heater in which the Au content of the first region of the Cu—Au braze part in contact with the Ni connection terminal falls within the range of more than 6 wt % to less than 10 wt %, the potential difference between the Ni connection terminal and the first region may be made smaller, and therefore, corrosion between the Ni connection terminal and the Cu—Au braze part may be suppressed to a greater extent than in a conventional ceramic heater. As a result, the corrosion resistance and endurance of the ceramic heater may be improved.

In the ceramic heater of the exemplary embodiment described above, the first region of the Cu—Au braze part in contact with the Ni connection terminal and having an Au content of more than 6 wt % to less than 10 wt % preferably has a specified thickness.

Therefore, in the exemplary embodiment, the Au content falls in the range of more than 6 wt % to less than 10 wt % in the first region of the Cu—Au braze part defined to be within a distance of 15 μm from a contact face with the Ni connection terminal (i.e., a thickness of 15 μm or less). In this manner, the potential difference between the Ni connection terminal and the first region is surely decreased, and the corrosion resistance and endurance of the ceramic heater is surely improved. The Au content falls in the range of more than 6 wt % to less than 10 wt % throughout the first region.

In order to attain an Au content of more than 6 wt % to less than 10 wt % in the first region, the Au content in the entire Cu—Au braze part may be set to more than 6 wt % to less than 10 wt %, but when the Au content in the entire Cu—Au braze part is within this range, the melting point of the braze alloy itself becomes very high. When such a braze alloy is used for brazing, the electrode pad, the Ni connection terminal and the like may react to change into an alloy during the brazing. Consequently, there is some concern that endurance may be lowered and, for example, the Ni connection terminal may fall off from the electrode pad. Therefore, the Au content in the entire Cu—Au braze part is preferably set to 10 wt % or more. Accordingly, the Au content of the first region alone needs to be lower than that of the entire Cu—Au braze part.

The present inventors have also found that the braze part in a second region (S in FIG. 7) disposed farther from the connection terminal than the first region, preferably has a gold content that is a maximum within the entire braze part.

Specifically, when the Au content of the second region farther from the connection terminal than the first region is maximized so as to move Cu originally present in the second region into the first region, the Au content in the first region alone may be made smaller than the Au content of the entire Cu—Au braze part. Further, since the second region is distant from the Ni connection terminal, there is no need to consider a potential difference between the Ni connection terminal and the second region. Yet further, there is no concern of causing corrosion in the second region between the Ni connection terminal and the Cu—Au braze part.

Cu originally present in the second region may move into the first region as follows: Since Cu has a closer property to Ni than Au (in comparing Cu and Au included in the Cu—Au braze part), Cu tends to concentrate toward the Ni connection terminal as compared with Au during brazing. Therefore, Cu may migrate into the first region due to this tendency. Specifically, while the Cu—Au braze part is in the form of a fluid before solidifying at a stage of forming the Cu—Au braze part, Cu moves from the second region into the first region in the Cu—Au braze part.

An entire portion farther from the connection terminal than the first region may be used as the second region, but the second region sufficiently has a thickness of 15 μm from the first region in the Cu—Au braze part along a direction away from the connection terminal (i.e., within a distance of 15 μm from the interface between the first region and the second region). In a third region farther from the connection terminal than the second region, the gold content preferably is substantially the same as the Au content of the entire Cu—Au braze part without Cu present therein moving into the first region.

Furthermore, through an experiment carried out by the present inventors, the Au content of the entire Cu—Au braze part has been found to be preferably 28 to 39 wt % in order to attain an Au content of more than 6 wt % and less than 10 wt % in the first region of the Cu—Au braze part in contact with the Ni connection terminal. Specifically, when the Cu—Au braze part is made of an alloy (a braze alloy) of Cu and Au having an Au content of 28 to 39 wt % and Cu originally present in the second region moves into the first region, the Au content in the first region may be made to fall within the range of more than 6 wt % and less than 10 wt %.

Alternatively, the gas sensor of the present invention includes a sensing element having a hollow cylindrical shape and a closed end, the sensing element extending along an axial direction; a metal shell that holds the sensing element; and the ceramic heater of the invention inserted into the sensing element. In this manner, the potential difference between the Ni connection terminal and the Cu—Au braze part may be made smaller, and hence, corrosion between the Ni connection terminal and the Cu—Au braze part may be suppressed as compared with a conventional gas sensor. Accordingly, a gas sensor in which the corrosion resistance and endurance of the ceramic heater are improved may be attained.

In addition, according to the exemplary embodiment, a method is provided for fabricating a ceramic heater including: a ceramic substrate having a heater element which generates heat when energized and an electrode pad disposed on a surface of the ceramic substrate, the electrode pad being electrically connected to the heater element; and a connection terminal electrically connected to the electrode pad through a braze part bonded to the electrode pad, the braze part being made of an alloy of copper and gold and the connection terminal being made of nickel or a nickel alloy, the method comprising: a brazing step of brazing the electrode pad and the connection terminal with each other through a braze alloy made of an alloy of copper and gold to form the braze part; and a heating step of heating at least the braze part at a temperature lower than a melting point of the braze alloy after the brazing step, wherein a first region of the braze part within a distance of 15 μm from a contact face between the braze part and the connection terminal has a gold content that is more than 6 wt % and less than 10 wt %.

When the heating step of heating at least the braze part at a temperature lower than the melting point of the braze alloy is performed after the brazing step, Cu originally present in a second region farther from the Ni connection terminal than a first region moves into the first region. As a result, the Au content may be made to fall within a range of more than 6 wt % to less than 10 wt % in the first region corresponding to a portion of the Cu—Au braze part that is within a distance of 15 μm from a contact face between the braze part and the Ni connection terminal. As a result, the potential difference generated between the Ni connection terminal and the first region is surely made smaller, and hence, the corrosion resistance and endurance of the ceramic heater is surely improved.

It should further be apparent to those skilled in the art that various changes in form and detail of the invention as shown and described above may be made. It is intended that such changes be included within the spirit and scope of the claims appended hereto.

The present application claims priority from Japanese Patent Application No. 2009-213250 filed on Sep. 15, 2009, and from Japanese Patent Application No. 2010-177043 filed on Aug. 6, 2010, the disclosures of which are incorporated herein by reference in their entirety.

What is claimed is:

1. A ceramic heater which comprises:
   a ceramic substrate having:
   a heater element which generates heat when energized; and
   an electrode pad disposed on a surface of the ceramic substrate, the electrode pad being electrically connected to the heater element, and
   a connection terminal electrically connected to the electrode pad through a braze part bonded to the electrode pad, the braze part being made of an alloy of copper and at least 28 wt % gold and the connection terminal being made of nickel or a nickel alloy,
   wherein a first region of the braze part within a distance of 15 μm from a contact face between the braze part and the connection terminal has a gold content of more than 6 wt % and less than 10 wt %, and
   wherein the braze part in a second region disposed farther from the connection terminal than the first region has a gold content that is a maximum gold content within the entire braze part.

2. A gas sensor comprising:
   a sensing element having a cylindrical shape and a closed end, said sensing element extending along an axial direction;
   a metal shell that holds the sensing element; and
   the ceramic heater as claimed in claim 1 inserted into the sensing element.

3. A method for fabricating a ceramic heater including: a ceramic substrate having a heater element which generates heat when energized; an electrode pad disposed on a surface of the ceramic substrate, the electrode pad being electrically connected to the heater element, and a connection terminal electrically connected to the electrode pad through a braze part bonded to the electrode pad, the braze part being made of an alloy of copper and at least 28 wt % gold and the connection terminal being made of nickel or a nickel alloy, the method comprising:
   brazing the electrode pad and the connection terminal with each other through a braze alloy made of an alloy of copper and gold to form the braze part; and
   heating at least the braze part at a temperature lower than a melting point of the braze alloy after the brazing step,
   wherein a first region of the braze part within a distance of 15 μm from a contact face between the braze part and the connection terminal has a gold content of more than 6 wt % and less than 10 wt %.

4. The method for fabricating a ceramic heater according to claim 3,
   wherein the braze part in a second region disposed farther from the connection terminal than the first region has a gold content that is a maximum gold content within the entire braze part.

* * * * *